(12) United States Patent
Krausman et al.

(10) Patent No.: US 6,529,752 B2
(45) Date of Patent: Mar. 4, 2003

(54) SLEEP DISORDER BREATHING EVENT COUNTER

(76) Inventors: David T. Krausman, 1706 Pine Forest Ct., Bel Air, MD (US) 21014; Richard P. Allen, 110 Glen Oban Dr., Arnold, MD (US) 21012

( * ) Notice: Subject to any disclaimer, the term of this patent is extended or adjusted under 35 U.S.C. 154(b) by 119 days.

(21) Appl. No.: 09/761,261

(22) Filed: Jan. 17, 2001

(65) Prior Publication Data

US 2002/0095076 A1 Jul. 18, 2002

(51) Int. Cl.[7] ................................................ A61B 5/00
(52) U.S. Cl. ....................... 600/323; 600/324; 600/340; 600/301; 600/484; 600/529
(58) Field of Search ................................ 600/323, 324, 600/340, 301, 309, 483, 484, 519, 522, 523, 529, 532, 533, 534, 538, 543, 595

(56) References Cited

U.S. PATENT DOCUMENTS

| | | | |
|---|---|---|---|
| 3,704,706 A | 12/1972 | Herczfeld et al. | 128/2 R |
| 3,998,550 A | 12/1976 | Konishi et al. | 356/39 |
| 4,086,915 A | 5/1978 | Kofsky et al. | 128/2 L |
| 4,266,554 A | 5/1981 | Hamaguri | 128/633 |
| 4,407,290 A | 10/1983 | Wilber | 128/633 |
| 4,759,369 A * | 7/1988 | Taylor | 600/323 |
| 4,955,379 A | 9/1990 | Hall | 128/633 |
| 5,025,791 A | 6/1991 | Niwa | 128/670 |
| 5,078,136 A | 1/1992 | Stone et al. | 128/633 |
| 5,368,026 A | 11/1994 | Swedlow et al. | 128/33 |
| 5,524,617 A * | 6/1996 | Mannheimer | 600/323 |
| 5,575,284 A | 11/1996 | Athan et al. | 128/633 |
| 5,632,272 A * | 5/1997 | Diab et al. | 600/323 |
| 5,645,060 A | 7/1997 | Yorkey | 128/633 |
| 5,662,106 A | 9/1997 | Swedlow et al. | 128/633 |
| 5,746,206 A * | 5/1998 | Mannheimer | 600/323 |
| 5,779,631 A | 7/1998 | Chance | 600/328 |
| 5,820,550 A | 10/1998 | Polson et al. | 600/323 |
| 5,853,364 A | 12/1998 | Baker et al. | 600/300 |
| 5,995,855 A * | 11/1999 | Kiani et al. | 600/323 |
| 6,095,991 A * | 8/2000 | Krausman et al. | 600/595 |
| 6,142,950 A * | 11/2000 | Allen et al. | 600/529 |
| 6,306,088 B1 * | 10/2001 | Krausman et al. | 600/301 |
| 6,342,039 B1 * | 1/2002 | Lynn et al. | 600/529 |
| 6,349,228 B1 * | 2/2002 | Kiani et al. | 600/323 |

* cited by examiner

Primary Examiner—Teresa Walberg
Assistant Examiner—Fadi H. Dahbour
(74) Attorney, Agent, or Firm—Larry J. Guffey (57) ABSTRACT

A method and a device for counting the number of sleep disordered breathing events experienced by a subject within a specified time period. Such a counter comprises: (1) an oxygen saturation level sensor for location at a prescribed site on the subject, (2) an oximetry conditioning and control module that controls the operation of the sensor and converts its output data to oxygen saturation level data, (3) a miniature monitoring unit having a microprocessor, a memory device, a timer for use in time-stamping data, a display means and a recall switch, and (4) firmware for the unit that directs: (i) the sampling and temporary storage of the oxygen saturation level data, (ii) the unit to analyze using a specified method the temporarily stored data to identify and count the occurrence of the subject's disordered breathing events, and to store the time of occurrence of each of these events, and (iii) the display means to display specified information pertaining to the counts in response to the actuation of the recall switch.

19 Claims, 8 Drawing Sheets

A METHOD FOR COUNTING THE NUMBER OF SLEEP DISORDERED BREATHING EVENTS EXPERIENCED BY A SUBJECT, WITHIN A SPECIFIED TIME PERIOD, COMPRISING THE STEPS OF:

(a) LOCATING AN OXYGEN SATURATION LEVEL SENSOR ON THE SUBJECT'S FINGER; THE SENSOR PROVIDING OUTPUT DATA THAT QUANTIFIES THE TEMPORAL VARIATION IN THE SUBJECT'S OXYGEN SATURATION LEVEL, THE SENSOR BEING CONNECTED TO AN OXIMETRY CONDITIONING AND CONTROL MODULE THAT CONTROLS THE OPERATION OF THE SENSOR AND CONVERTS ITS SENSOR OUTPUT INTO OXYGEN SATURATION LEVEL DATA, THE MODULE BEING CONNECTED TO A MINIATURE MONITORING UNIT HAVING A MICROPROCESSOR, A MEMORY DEVICE, A TIMER FOR USE IN TIME-STAMPING DATA, A DISPLAY MEANS, A RECALL SWITCH, AND SPECIFIED FIRMWARE FOR CONTROLLING THE OPERATION OF THE UNIT, (b) SAMPLING THE OXYGEN SATURATION LEVEL DATA AT A SAMPLING FREQUENCY OF ONE SAMPLE PER SECOND.

(c) TEMPORARILY STORING THE SAMPLED DATA IN THE MEMORY DEVICE, (d) ANALYZING THE TEMPORARILY STORED DATA TO IDENTIFY AND COUNT THE OCCURRENCE OF THE SUBJECT'S DISORDERED BREATHING EVENTS, WHEREIN THE ANALYSIS METHOD ENTAILS: (i) ESTABLISHING A TEMPORALLY-MOVING BASELINE FOR THE OXYGEN SATURATION LEVEL DATA, AND (ii) IDENTIFYING A DISORDERED BREATHING EVENT TO HAVE OCCURRED WHEN THE DATA DECREASES BY 3% OR MORE FROM THE TEMPORALLY-MOVING BASELINE VALUE, (e) STORING IN THE MEMORY DEVICE THE TIME OF OCCURRENCE OF EACH OF THE SUBJECT'S DISORDERED BREATHING EVENTS, (f) DISPLAYING SPECIFIED INFORMATION PERTAINING TO THE COUNTS IN RESPONSE TO THE ACTUATION OF THE RECALL SWITCH, WHEREIN THIS SPECIFIED INFORMATION MAY INCLUDE: (i) THE TOTAL NUMBER OF COUNTS ACCUMULATED IN A SPECIFIED TIME PERIOD, OR (ii) THE NUMBER OF COUNTS ACCUMULATED DURING EACH OF A SPECIFIED NUMBER OF INTERVALS COMPRISING THE TIME PERIOD.

SLEEP DISORDER BREATHING EVENT COUNTER

STATEMENT OF FEDERAL SUPPORT

The present invention was made with Federal Government support (2R43HL62077-02) awarded by The National Heart, Lung and Blood Institute. Accordingly, the Federal Government has certain rights in this invention.

BACKGROUND OF THE INVENTION

1. Field of the Invention

This invention relates to the use of pulse oximeters and methods for monitoring the occurrences of a patient's sleep disorder breathing events. More particularly, this invention relates to a device and method for monitoring oxygen desaturations in a subject's arterial blood flow (oximetry) as a result of sleep apnea events and other respiratory disturbances, and counting the number of these events that occur during a prescribed period.

2. Description of the Related Art

The diagnosis of a patient's sleep disorders typically involves an analysis of the patient's breathing disturbances during his or her sleep. These breathing disturbances are defined by the American Sleep Disorder Association and the American Sleep Apnea Association as being sleep "apnea" if the disordered breathing is a pause that lasts ten or more seconds. They are further identified as: (1) Central Apnea—cessation of airflow (upper airway—oral and nasal) and respiratory effort (amplitude of chest movement during breathing); (2) Obstructive Apnea—cessation of airflow with continuation of respiratory effort; (3) Hypopnea—decrease in airflow from baseline (typically one-third to one-half or more) with continuation of normal or decreased levels of respiratory effort; and (4) Cheyne-Stokes Breathing—a breathing pattern that characteristically shows cyclical breathing with progressively decreasing breathing to a shallow level followed by progressively increasing breathing in a decrescendo-crescendo pattern. During the shallow breathing period the decreases may be severe enough to be clear central hypopneas or apneas which last for several seconds. Such apnea events may occur hundreds of times during the sleep period and may lead to severe sleep disruptions and frequent awakenings.

The analysis and diagnosis of respiratory sleep pathologies currently involve a comprehensive testing method utilizing polysomnography (PSG). This procedure involves a full night testing in a medical sleep laboratory to monitor the temporal variations in the amplitude of the patient's sleep-impacted, physiological parameters, including: a continuous measure of the level of oxygen saturation in the arterial blood flow (SpO2), heart rate, upper respiratory airflow, thorax and abdomen respiration efforts, electroencephalograms (EEG; electrical activity of the brain), electro-oculogram (EOG; electrical activity related to movement of the eyes), and electromyograms (EMG; electrical activity of a muscle). The PSG testing procedures are expensive as they are typically conducted in clinical settings by trained PSG technicians.

Current PSG equipment used for sleep testing share common, less-than-desirable features: (1) their use is expensive, since the equipment itself is expensive and a technician usually must be involved for its set-up and disconnection, plus the data collected must be subjectively analyzed by highly trained, sleep professionals, and (2) the recording devices require patients to be outfitted with tethered sensors for connection to bulky body monitors, computers or consoles such as a polygraph, thus, their size and weight does not allow the patient to be ambulatory, which can be essential for the evaluation of treatment efficiency and compliance.

Although PSG testing is the standard method establish for testing sleep disordered patients, there is strong evidence that measurements of the level of oxygen saturation in a subject's arterial blood flow (SpO2) alone is useful for assessing a patient's sleep-related, breathing disturbances. A compilation of several recent studies, which observed over seven thousand patients suspected or diagnosed with sleep apnea, reported typical oxygen levels decreases of anywhere form 2% to 4% for hypopneas (Note: The average oxygen saturation (profusion) baseline, measured at the finger of a subject, typically ranges from 92% to 98%). Some patients with central or obstructive apneas have been noted to experience arterial blood oxygen saturation decreases greater than 30%.

Oxygen desaturation events of ten seconds or longer duration and having a oxygen level decrease of 3% or more would appear to be a viable means for diagnosing the occurrence of a sleep hypopnea. See FIG. 1.

Such measurements of the level of oxygen saturation in a subject's arterial blood flow (SpO2) are typically made with commercially-available pulse oximeters. Pulse oximetry has previously been described in many U.S. Patents, including U.S. Pat. Nos. 4,407,290, 4,266,554, 4,086,915, 3,998,550, and 3,704,706.

As blood is pulsed through the lungs by the heart action, a certain percentage of the deoxyhemoglobin, RHb, picks up oxygen so as to become oxyhemoglobin, HbO2. From the lungs, the blood passes through the arterial system until it reaches the capillaries at which point a portion of the HbO2 gives up its oxygen to support the life processes in the adjoining cells.

By medical definition, the oxygen saturation level is the percentage of HbO2 over the total hemoglobin; therefore, SpO2=HbO2/(RHb+HbO2). A person can lose consciousness or suffer permanent brain damage if the person's oxygen saturation value falls to very low levels for extended periods of time. Because of the importance of the oxygen saturation value, it has been referred to as the fifth vital sign.

An oximeter determines the blood's saturation value by analyzing the change in color of the blood. When radiant energy passes through a liquid, certain wavelengths may be selectively absorbed by particles which are dissolved therein. For a given path length that the light traverses through the liquid, Beer's Law (the Beer-Lambert or Bouguer-Beer relation) indicates that the relative reduction in radiation power at a given wavelength is an inverse logarithmic function of the concentration of the solute in the liquid that absorbs that wavelength.

For a solution of oxygenated human hemoglobin, the absorption maximum is at a wavelength of about 640 nanometers (red), therefore, instruments that measure absorption at this wavelength are capable of delivering clinically useful information as to the oxyhemoglobin levels.

In general, noninvasive methods for measuring oxygen saturation in arterial blood utilize the relative difference between the electromagnetic radiation absorption coefficient of deoxyhemoglobin, RHh, and that of oxyhemoglobin, HbO2. It is well known that deoxyhemoglobin molecules absorb more red light than oxyhemoglobin molecules, and that absorption of infrared electromagnetic radiation is not affected by the presence of oxygen in the hemoglobin molecules. Thus, both RHb and HbO2 absorb electromagnetic radiation having a wavelength in the infrared region to approximately the same degree. However, in the visible region, the light absorption coefficient for RHb is quite different from the light absorption coefficient of HbO2 because RHb absorbs significantly more light in the visible spectrum than HbO2.

In the practice of pulse oximetry techniques, the oxygen saturation of hemoglobin in intravascular blood is determined by: (1) alternately illuminating a volume of intravascular blood with electromagnetic radiation of two or more selected wavelengths (e.g., a red wavelength and an infrared wavelength), (2) detecting the time-varying electromagnetic radiation intensity transmitted through or reflected back by the intravascular blood for each of the wavelengths, and (3) calculating oxygen saturation values for the patient's blood by applying the Lambert-Beer transmittance law to the detected transmitted or reflected electromagnetic radiation intensities at the selected wavelengths.

Today's conventional pulse oximeters generally are complex, table-top consoles or handheld devices. They are commercially available from many sources, including: Nonin (#8500 model), HealthDyne (#920M), Vitalog (#VX4), Novametrix (#510/511), Allied Healthcare (#3520), Criticare Systems (#5040), Lifecare International (SpotChek+), Datex-Ohmeda (#3900), Palco Labs (#300/340/400), Nellcor/EdenTec (#N-20/N-30), and Respironics (Cricket).

The accuracy of these devices is often plagued by the effects of motion artifacts which tend to cause erroneous oxygen desaturation measurements. However, the accuracy of such measurement may be improved by employing bandpass or digital filtering of the SpO2 signal.

Other filtering technologies, such as that described as "Masimo Set", are employed by Ivy (#2000), Allegiance Oxi-Reader (#M2000-US), Quartz Medical (#Q-400) and others. These rely on a combination of a special probe sensor and an adaptive filtering technique to cancel motion artifacts. Meanwhile, another oximeter by SIMS BCI (#3404-000) uses serial autocorrelation technology to reduce the effects of motion artifacts.

Despite many advances in pulse oximetry, current oximeters are still bound by several major limitations, including: (1) their use of long tethers from the finger probe to the console which typically introduces artifact and signal inaccuracies, (2) the requirement for the presence of a trained professional to direct their set-up and use, (3) the typical restriction of their use to clinical or hospital environments, (4) their typical use with cumbersome console recording units that limit a patient's mobility, (5) their output typically being provided in the form of temporal displays of a patient's trends or average oxygen levels, and, most importantly for sleep medicine purposes, (6) they do not count and display, in real-time, the number of oxygen desaturations events experienced by a patient due to his/her disordered breathing events or disturbances during a prescribed time period.

Thus, an improved type of oximeter having the novel capability of providing counts of respiratory interruptions and disturbances would be a valuable contribution to sleep medicine. It would provide a less expensive alternative to PSG, and provide a relatively easy to use means for home monitoring of a patient's sleep.

Additionally, with capability for unattended, ambulatory use, such an improved monitoring device would provide a preliminary screening alternative for assisting with the diagnosis of patients suffering from sleep disorders. For example, a device, that provides information as to which patients might benefit the most from complete PSG testing, could contribute greatly by effectively expanding the audience to whom PSG testing would be available.

SUMMARY OF THE INVENTION

Recognizing the need for a much simpler device and method for diagnosing sleep disorders, the present invention is generally directed to satisfying the needs set forth above and the problems identified with prior testing systems for assessing respiratory disturbances during sleep. The problems associated with the expense of PSG testing, its utilization only in clinical environments, the limited number of patients who are being assessed for sleep disorder breathing with PSG testing, and the non-ambulatory nature of such testing are resolved by the present invention.

In accordance with one preferred embodiment of the present invention, the foregoing need can be satisfied by providing a sleep disorder breathing event counter for counting the total number of sleep disordered breathing events experienced by the subject during a sleep period. This battered powered counter comprises: (1) an oxygen saturation level sensor for location at a prescribed site on the subject, with the sensor providing output data that quantifies the temporal variation in the subject's oxygen saturation level at the prescribed site, (2) an oximetry conditioning and control module that controls the operation of the sensor and converts the sensor's output signal to oxygen saturation data, (3) a miniature monitoring unit having a microprocessor with a memory device, a timer for use in time-stamping data, a display means and a recall switch, and (4) firmware integral to the microprocessor that directs the (i) sampling of the oxygen saturation data provided by the oxygen sensor conditioning and control module at prescribed time intervals, (ii) temporary storing of the oxygen saturation data in a designated area, buffer, of the memory device, (iii) the unit to analyze the temporarily stored data to detect an oxygen saturation decrease (desaturation) below a specified level (typically 3% or greater) from its baseline value, with such a decrease being the assumed definition of a disordered breathing event, (iv) storing time-stamped data corresponding to each of these events, (v) analyzing the stored, time-stamped data to count the total number of disordered breathing events that occurred during the subject's sleep period, and (vi) the display means to display specified information pertaining to the counts in response to the actuation of the recall switch.

In another preferred embodiment, the present invention is seen to take the form of a method for counting the number of sleep disordered breathing events experienced by a subject within specified periods of sleep. For example, the number of disordered breathing events that occurred per hour during the sleep period. This method comprises the steps of: (1) locating an oxygen saturation level sensor at a prescribed site on the subject, the sensor providing output data that quantifies the temporal variation in the subject's oxygen saturation level at the prescribed site, the sensor being connected to an oximetry conditioning and control module that controls the operation of the sensor and converts the sensor output data to oxygen saturation level data, the module being connected to a miniature monitoring unit having a microprocessor, a memory device, a timer for use in time-stamping data, a display means, a recall switch, and specified firmware for controlling the operation of the unit, (2) sampling the oxygen saturation level data at a prescribed frequency, (3) temporarily storing the sampled data in the memory device, (4) analyzing with a specified method the temporarily stored data to identify and count the occurrence of the subject's disordered breathing events, (5) storing in the memory device the time of occurrence of each of the disordered breathing events, and (6) displaying specified information pertaining to the counts in response to the actuation of the recall switch.

Thus, there has been summarized above, rather broadly, the more important features of the present invention in order that the detailed description that follows may be better understood and appreciated. There are, of course, additional features of the invention that will be described hereinafter and which will form the subject matter of any eventual claims to this invention.

In this respect, before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is therefore an object of the present invention to provide a device and method that can be used for counting in real-time the number of significant oxygen desaturation events that occur during a subject's sleep.

It is another object of the present invention to provide a device and method that will advance the utility of pulse oximetry technology as applied to sleep medicine.

It is a further object of the present invention to provide a device and method for advancing the diagnostic capabilities of health practitioners in the field of sleep medicine.

It is yet another object of the present invention to provide a device and method that will further allow for the monitoring of the occurrence of a subject's sleep disordered breathing events in the subject's unattended, home environment.

These and other objects and advantages of the present invention will become is readily apparent as the invention is better understood by reference to the accompanying drawings and the detailed description that follows.

BRIEF DESCRIPTION OF THE DRAWINGS

FIG. 1 displays a schematic flow diagram which depicts a method in accordance with a preferred embodiment of the present invention.

DESCRIPTION OF THE PREFERRED EMBODIMENT

Referring now to the drawings wherein are shown preferred embodiments and wherein like reference numerals designate like elements throughout, there is shown in FIG. 1 a schematic flow diagram which depicts a method in accordance with a preferred embodiment of the present invention.

Figure 1A:
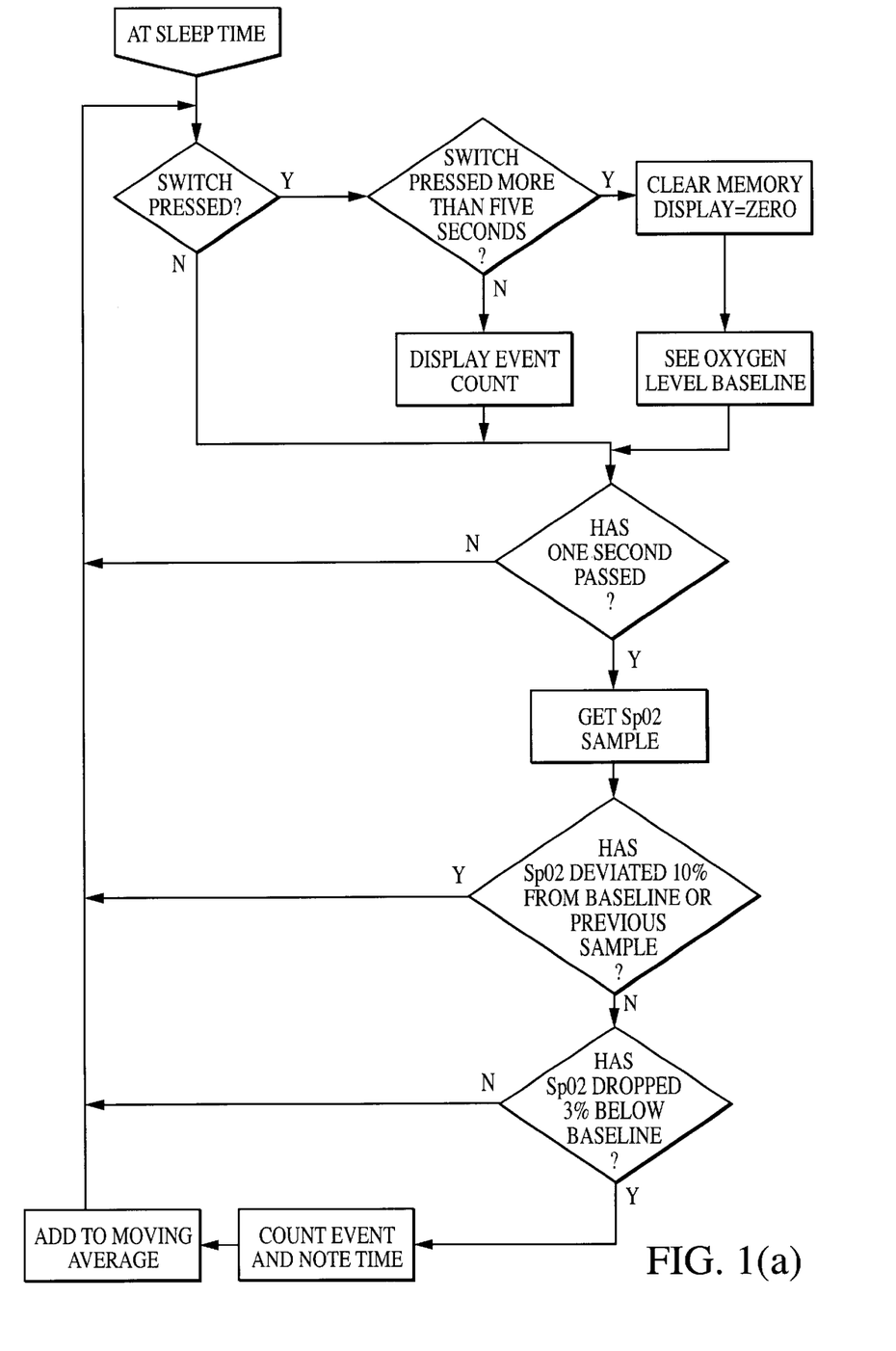
FIG. 1(a) illustrates a flow diagram of the firmware algorithm that: (i) interrogates the SpO2 signal once per second, and (ii) determines if the SpO2 is a movement or other artifact (10% drop or greater from average baseline), or if the SpO2 value is a valid oxygen desaturation event (3% or greater drop from the average baseline), adds the current SpO2 sample to the moving eight sample average.

In this embodiment, the method is seen to comprise the steps of:

(a) using a commercial oxygen saturation sensor to measure in the frequency range of 0.2 to 5.0 data points per second, preferably one data point per second, the temporal variations in a subject's oxygen saturation levels. The sensor, such as a NONIN 9000A, is connected to an oxygen sensor conditioning and control module, such as a NONIN #2332-000, for providing serial SpO2 output at a specified rate, preferably one data value per second. This output is inputted into a miniature, self-contained, battery-operated, microprocessor-based monitoring unit. The monitoring unit additionally contains embedded firmware, an off-chip memory device, a time-of-day clock or timer for use in time-stamping data, a display means and a push-button recall switch, (b) initialzing the monitoring unit by holding the recall switch in a depressed position for a specified period, preferably five seconds or greater, wherein the memory will be cleared of previous data, the display counter reset to zero, with this action being implemented just before the subject's sleep period begins, (c) using the microprocessor to sample the serial SpO2 oxygen saturation data once per second, wherein a temporally-moving baseline average is established by at any instant averaging the immediately previous, eight SpO2 data points, (d) using firmware, as shown in FIG. 1(a), to: (i) identify and reject data samples containing signal artifacts resulting from probe motion. This is accomplished by means of interrogating each SpO2 sample, then defining those samples that deviate 10% or greater from the baseline of the previous sample to be such artifacts and rejecting them, (ii) identify the occurrence of an oxygen saturation decrease of a prescribed percentage, preferably 3% or more from the moving baseline, as being defined as representing a valid disordered breathing event. Upon such an identification, the display's counter is incremented one count so that the display counter keeps a running tally of such identified events, and the event and time of the event are stored in memory for later recall, and (iii) direct the microprocessor to receive a command when the recall switch is actuated so as to display the count of the number of the subject's disordered breathing events so identified during the specified sleep period, where, for example, pressing (for less than 5 seconds) and releasing the monitoring unit's recall switch causes the unit's display means to display the number of disordered breathing events that occurred during the first hour after initialization of the unit, wherein pressing and releasing the switch a second time provides the number of disordered breathing events that occurred during the second hour of the sleep period; with this data recall process being repeatable for each hour of the sleep period.

Figure 2:
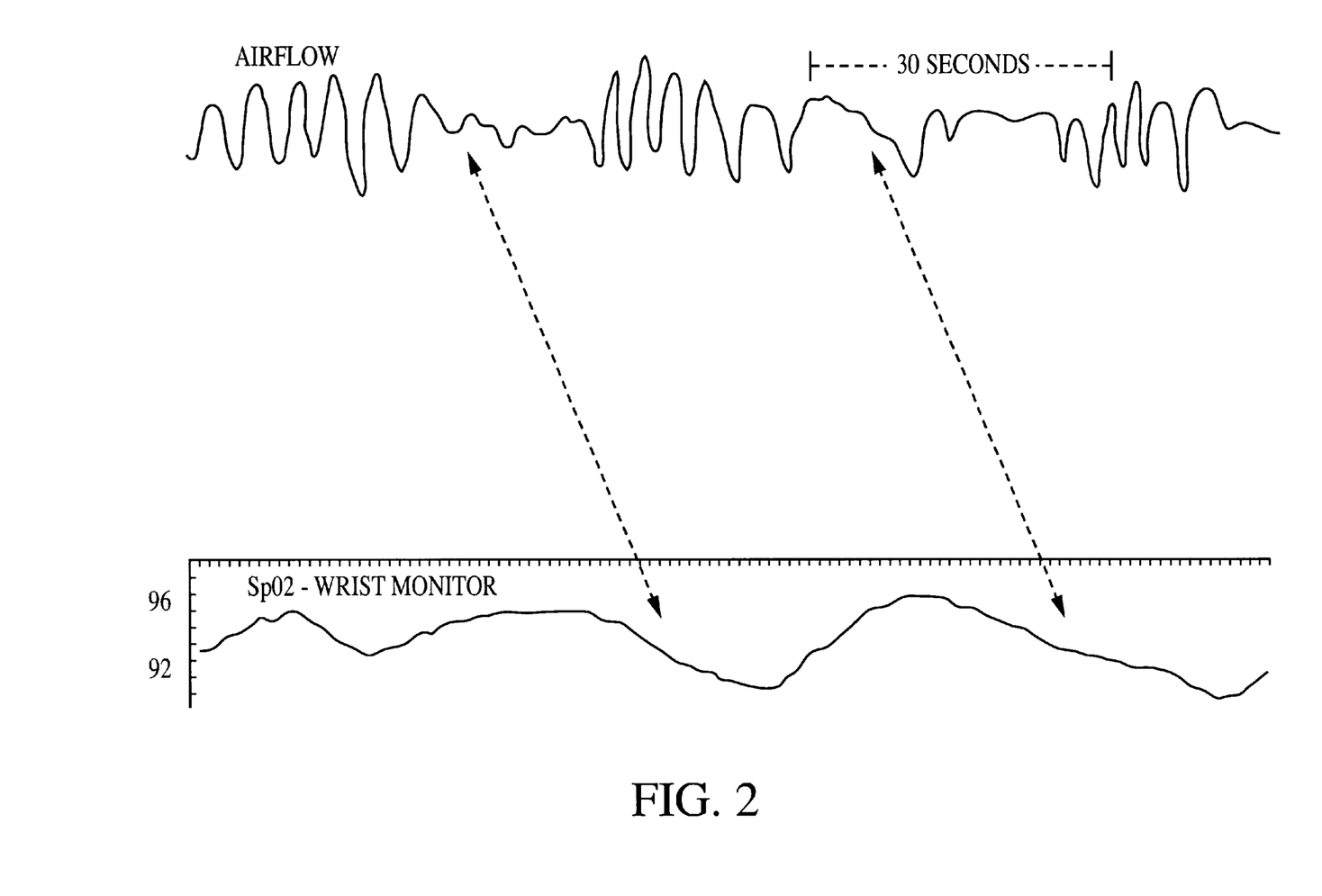
FIG. 2 shows polygraph tracings of experimentally-determined effects of oxygen desaturation events in the arterial blood (SPO2 bottom tracing) of a subject due to interruptions of normal breathing during periods of sleep. The airflow signal (top tracing) was derived from an oral/nasal thermocouple sensor and depicts the subject's interruptions of breathing (reduced airflow signal amplitude). The 10 to 15 second delay from cessation of breathing to the corresponding SpO2 desaturation event is a measure of how fast the subject's blood circulation responds to a respiratory disturbance. See dotted line showing delayed response.

In another preferred embodiment, the present invention is a sleep disorder breathing event counter 1. The occurrence of a subject's sleep disordered breathing events are identified by analyzing the corresponding oxygen desaturation events occurring in the subject's arterial blood flow. See FIG. 2.

Figure 3:
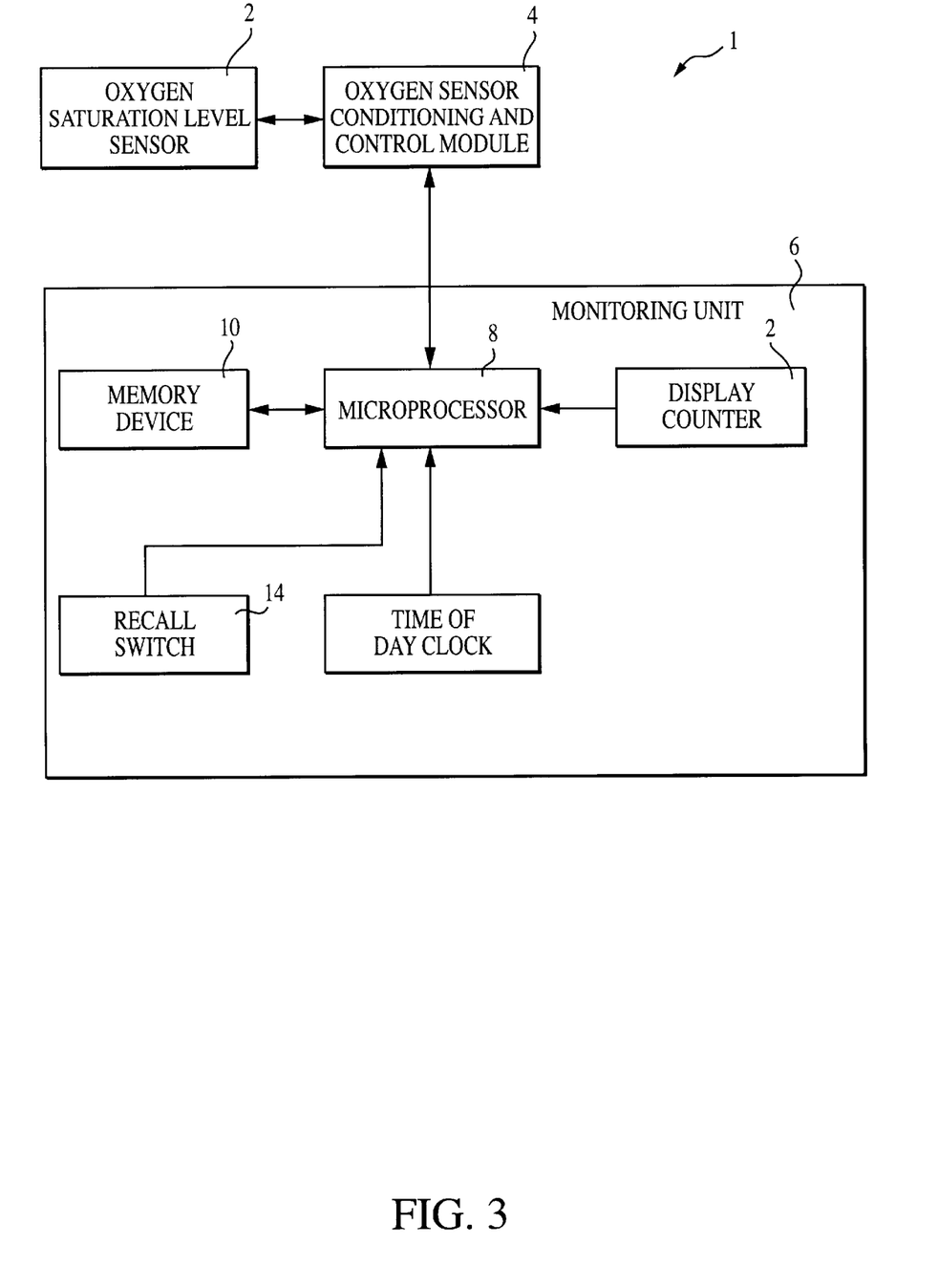
FIG. 3 is a schematic diagram of a preferred embodiment of the present invention.

In this embodiment, a commercial, oxygen saturation sensor 2, such as a NONIN #9000A, as schematically shown in FIG. 3, measures the temporal variations in a subject's oxygen saturation levels. This sensor 2 is connected to an oxygen sensor conditioning and control module 4, such as a NONIN #2332-000, which provides serial SpO2 output data to a miniature, self-contained, monitoring unit 6 which samples the oxygen saturation data at a prescribed time interval.

The monitoring unit 6 includes a microprocessor 8 with embedded firmware and a means of filtering out movement artifact which may cause disturbances in the oxygen saturation level readings which would otherwise be erroneously interpreted as the subject experiencing a disordered breathing event. While various filtering methods have been found to diminish measurement error as the result of probe motion, the present invention utilizes a real-time, digital filter algorithm contained within the memory of the microprocessor to improve signal-to-noise ratio, thereby reducing the effects of probe motion artifacts.

The microprocessor 8 has internal embedded firmware which includes an algorithm that characterizes the detected oxygen desaturation episodes as being attributable to various types of apnea and other restricted breathing events. The monitoring unit 6 also contains an integrated memory device 10 that is used to time-stamp and store the occurrence of each detected, disordered breathing event.

A counter or other display means 12 is used to visually display, in real-time, a tally of the total number of disordered breathing events experienced by the subject. A switch 14 is provided to allow the subject to recall and visually display the number of disordered breathing events occurring per hour or other prescribed time period.

Figure 4:
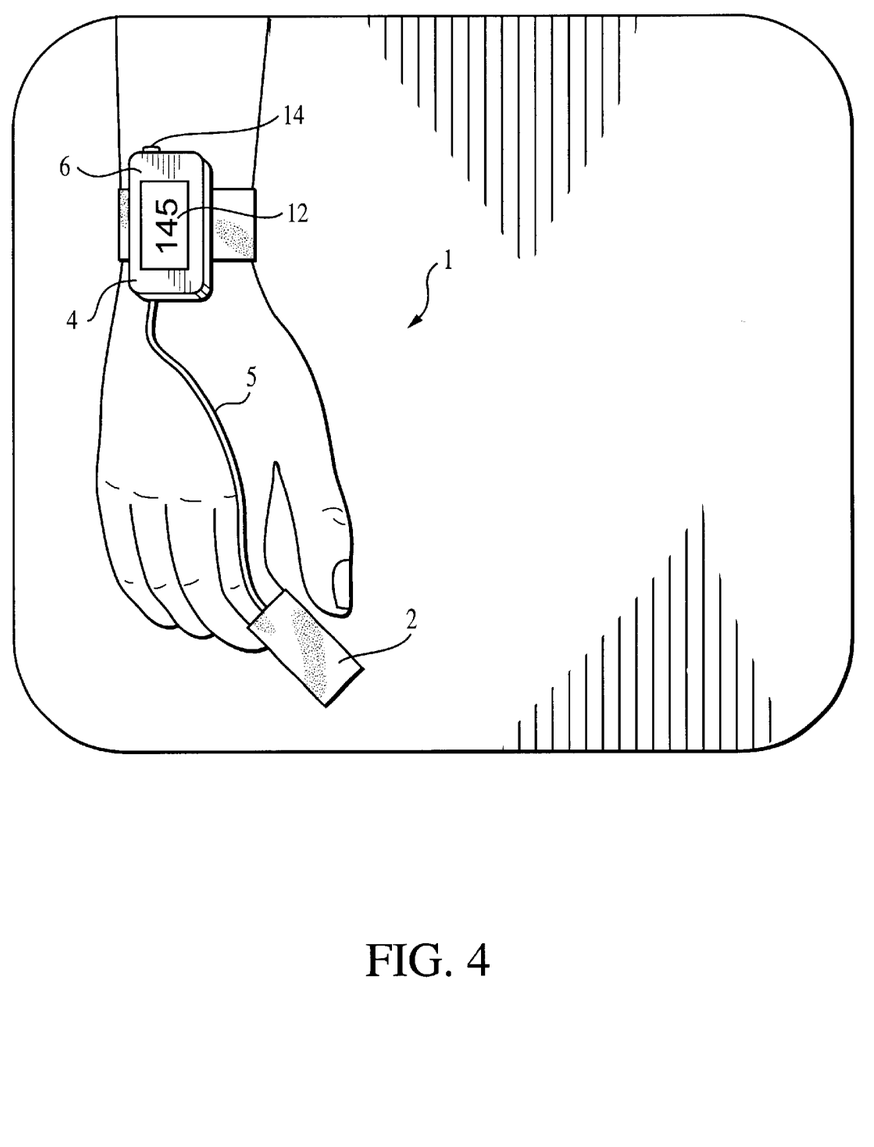
FIG. 4 illustrates the placement of the embodiment of FIG. 3 onto the wrist and finger of a subject.

FIG. 4 illustrates one option for the placement of this embodiment of the present invention on a patient whose time-varying oxygen saturation levels are to be monitored. The patient is seen to wear on his/her wrist a housing, containing all the elements of the present invention. A self-applied, low-cost, oximetry probe, containing the sensor 2, is applied to the subject's index finger. The oximetry probe is connected to the control module 4 and monitoring unit 6 by a short cable 5.

The present invention uses a commercial oximetry probe with a NONIN #2332-000 oximetry conditioning module 4 to calculate SpO2 based on the principle that deoxygenated and oxygenated hemoglobin have markedly different light absorption characteristics.

The probe sensor 2 contains two light emitting diodes (LEDs) and a photodetector sensor. The photodetector and LEDs are placed opposite one another across a pulsatile vascular bed, such as the finger or earlobe. One light source emits light at red (typically 660 nanometers (nm)) and the other infrared (typically 815–940 nm) wavelengths. The diodes switch on and off alternately (typically 200 to 2,000 times per second) enabling the photodetector to measure the transmitted light several hundred or thousand times per second.

As a general rule, a time multiplexed approach is used to translate the signals into a plethysmographic waveform which consists of a minimum of three operational elements: active red, active infrared, and a dark phase in which the ambient light is measured by the photodetector. The major variable affecting absorption is due to pulsatile oxygen saturation level changes.

Most commercial pulse oximeters use fixed or adjustable signal averaging techniques. The oximeter's ability to indicate a desaturation trend is one of its main advantages. However, the response time of an oximeter depends on the number of data points averaged before the saturation reading is displayed. Averaging algorithms, closely guarded by manufacturers, determine the response time of the oximeter which reduces the instrument's ability to report short transient changes in oxygen saturation levels. Thus, present day oximeters typically produce output readings that indicate a trend or percentage of oxygen saturation over an averaged period of time.

The current direction of sleep disorders medicine emphasizes early detection of mild sleep disordered breathing events such as short apnea events which often leads to sleep disruption. Detecting even small, short desaturation events is critical for sleep medicine and is obscured by the current use of signal averaging techniques for oximeters.

Figure 5A:
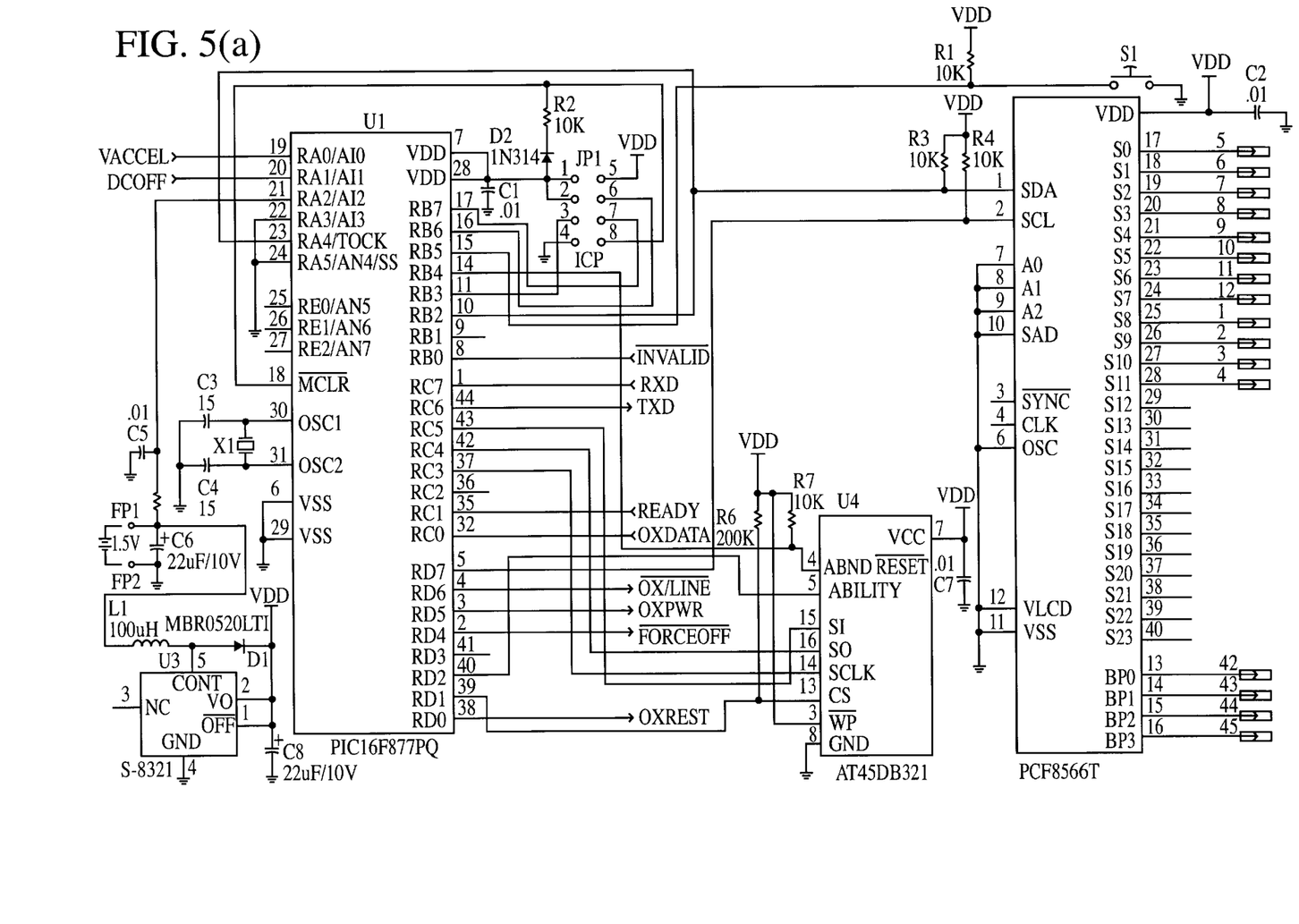
FIGS. 5(a)–(c) is a schematic circuit diagram of the embodiment shown in FIG. 3.
Figure 5B:
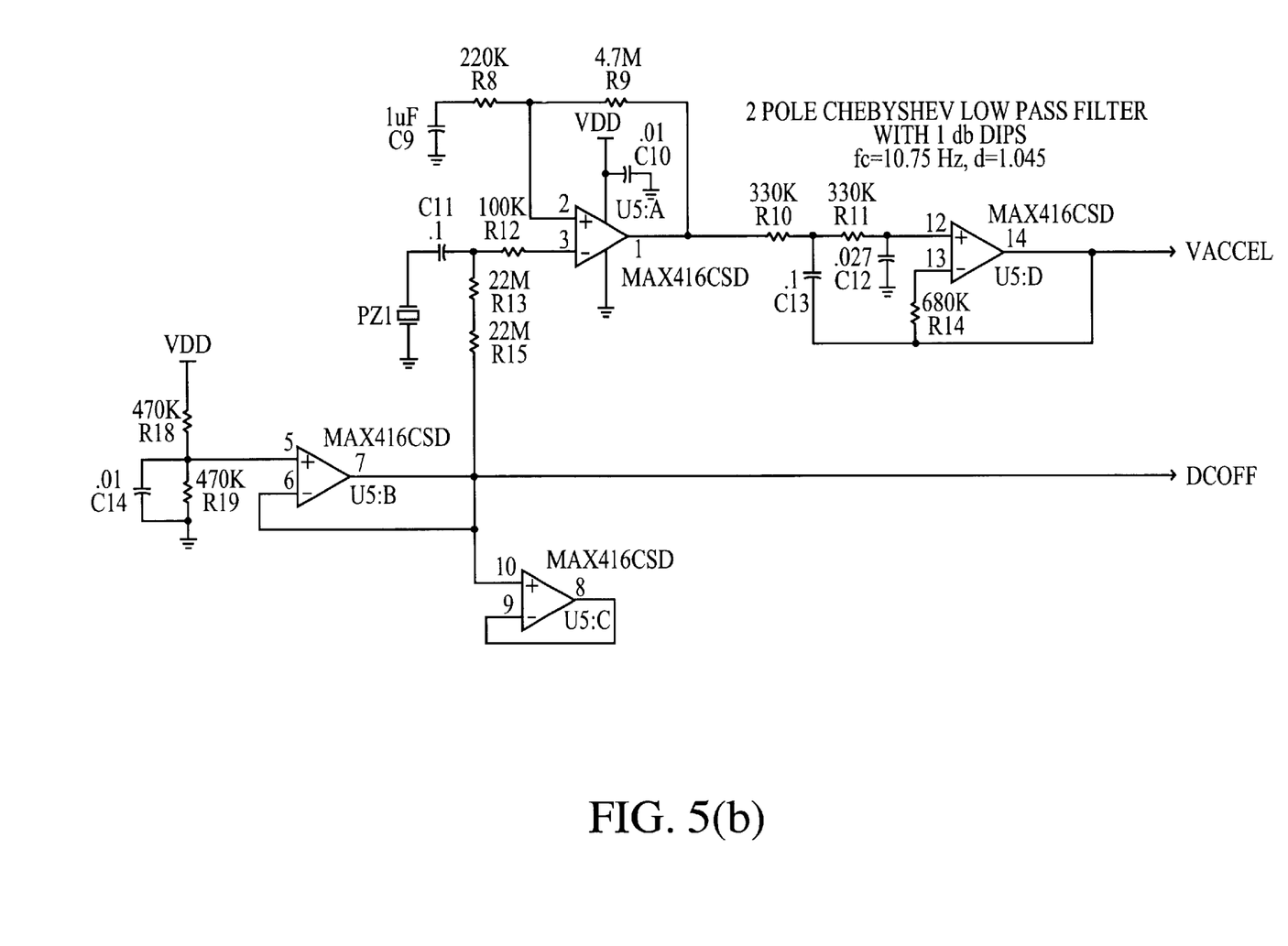
Figure 5C:
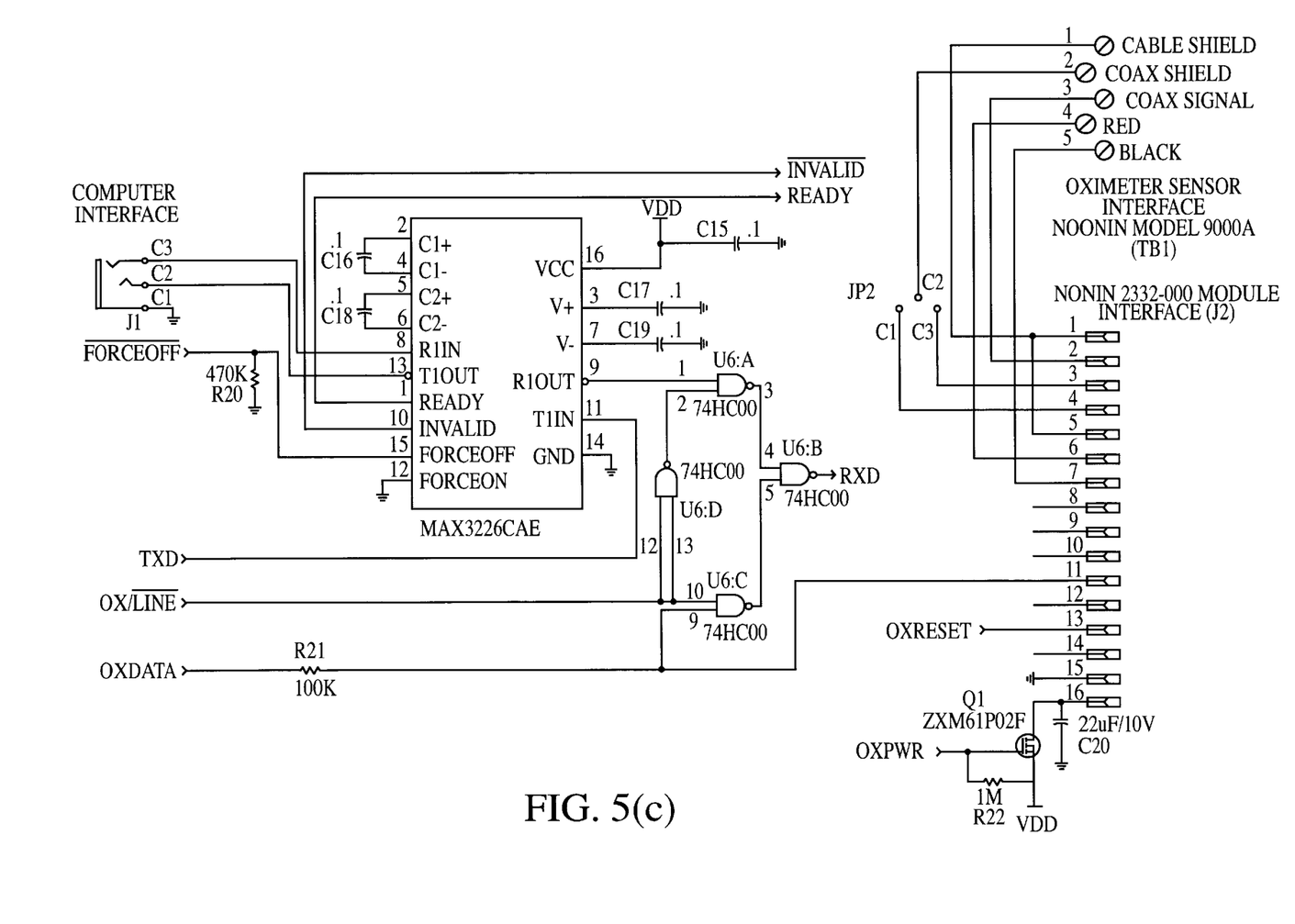

Additional appropriate hardware for use in the present invention as shown in FIGS. 5(a)–(c). It includes: (1) printed circuit boards of four-layer, through-hole design for surface mount technology (SMT) components, (2) an ultra-low power CMOS microprocessor (Microchip PIC 16F877PQ microprocessor or similar) with support chips for timing, control and with programmable nonvolatile FLASH memory, the microprocessor containing: (i) a serial input port for receiving the SpO2 data from the NONIN conditioning module, (ii) firmware for the microprocessor to receive the SpO2 data, (iii) control firmware for the microprocessor for storing real-time sampled data (typically once per second) for interpretation and apnea detection, (3) an LCD readout display to indicate a count of total apnea events, or the number of apnea events per hour, (4) a switch to recall the apnea events per hour for display, and (5) a replaceable AA battery cell providing ample power (minimum of 8 hours) for a single night's recording session.

Battery power for portable oximeters can present a major limiting factor for home recording. Especially, for battery powered handhelds since tabletop models and some bedside units use household line power. Most handhelds rely on heavy batteries (usually 6–8 AA cells) to supply power The present invention has been designed for ease of battery replacement and does not require any specific action or setup by the to-be-monitored subject.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. A sleep disorder breathing event counter for counting the number of sleep disordered breathing events experienced by a subject within a specified time period, said counter comprising:

an oxygen saturation level sensor for location at a prescribed site on said subject, said sensor providing output data that quantifies the temporal variation in the subject's oxygen saturation level at said prescribed site, an oximetry conditioning and control module connected to said sensor that controls the operation of said sensor and converts said sensor output data to oxygen saturation level data, a miniature monitoring unit connected to said module, said unit having a microprocessor, a memory device, a timer for use in time-stamping data, a display means and a recall switch, and firmware for said unit that directs: (i) the sampling of said oxygen saturation level data at a prescribed frequency and temporarily stores said data in said memory device, (ii) said unit to analyze using a specified method said temporarily stored data to identify and count the occurrence of said subject experiencing disordered breathing events, and to store in said memory device the time of occurrence of each of said events, and (iii) said display means to display specified information pertaining to said counts in response to the actuation of said recall switch.

2. A sleep disorder breathing event counter as recited in claim 1, wherein said prescribed site is said subject's finger.

3. A sleep disorder breathing event counter as recited in claim 2, wherein said prescribed sampling frequency is in the range of 0.2 to 5.0 data points per second.

4. A sleep disorder breathing event counter as recited in claim 3, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

5. A sleep disorder breathing event counter as recited in claim 2, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

6. A sleep disorder breathing event counter as recited in claim 2, wherein said specified information is chosen from the group consisting of: (i) the total number of counts accumulated in a specified time period, or (ii) the number of counts accumulated during each of a specified number of intervals comprising said time period.

7. A sleep disorder breathing event counter as recited in claim 1, wherein said prescribed sampling frequency is in the range of 0.2 to 5.0 data points per second.

8. A sleep disorder breathing event counter as recited in claim 7, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

9. A sleep disorder breathing event counter as recited in claim 1, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

10. A sleep disorder breathing event counter as recited in claim 9, wherein said specified information is chosen from the group consisting of: (i) the total number of counts accumulated in a specified time period, or (ii) the number of counts accumulated during each of a specified number of intervals comprising said time period.

11. A sleep disorder breathing event counter as recited in claim 1, wherein said specified information is chosen from the group consisting of: (i) the total number of counts accumulated in a specified time period, or (ii) the number of counts accumulated during each of a specified number of intervals comprising said time period.

12. A method for counting the number of sleep disordered breathing events experienced by a subject within a specified time period, said method comprising the steps of:

locating an oxygen saturation level sensor at a prescribed site on said subject, said sensor providing output data that quantifies the temporal variation in the subject's oxygen saturation level at said prescribed site, said sensor being connected to an oximetry conditioning and control module that controls the operation of said sensor and converts said sensor output data to oxygen saturation level data, said module being connected to a miniature monitoring unit having a microprocessor, a memory device, a timer for use in time-stamping data, a display means, a recall switch, and specified firmware for controlling the operation of said unit, sampling said oxygen saturation level data at a prescribed frequency, temporarily storing said sampled data in said memory device, analyzing in a specified manner said temporarily stored data to identify and count the occurrence of said subject experiencing disordered breathing events, storing in said memory device the time of occurrence of each of said disordered breathing events, and displaying specified information pertaining to said counts in response to the actuation of said recall switch.

13. A method for counting a subject's sleep disordered breathing events as recited in claim 12, wherein said prescribed site is said subject's finger.

14. A method for counting a subject's sleep disordered breathing events as recited in claim 12, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

15. A method for counting a subject's sleep disordered breathing events as recited in claim 12, wherein said specified information is chosen from the group consisting of: (i) the total number of counts accumulated in a specified time period, or (ii) the number of counts accumulated during each of a specified number of intervals comprising said time period.

16. A sleep disorder breathing event counter for counting the number of sleep disordered breathing events experienced by a subject within a specified time period, said counter comprising:

a means for measuring the oxygen saturation level at a prescribed site on said subject, said means providing output data that quantifies the temporal variation in the subject's oxygen saturation level at said prescribed site, a means for sampling said oxygen saturation level data at a prescribed frequency, a means for temporarily storing said sampled data, a means for analyzing using a specified method said temporarily stored data to identify and count the occurrence of said subject's disordered breathing events, a means for storing and counting the time of occurrence of each of said disordered breathing events, and a means for displaying specified information pertaining to said counts of disordered breathing events.

17. A sleep disorder breathing event counter as recited in claim 16, wherein said prescribed site is said subject's finger.

18. A sleep disorder breathing event counter as recited in claim 16, wherein said specified analysis method involves: (i) establishing a temporally-moving baseline for said oxygen saturation level data, and (ii) identifying a disordered breathing event to have occurred when said data decreases by a prescribed percentage from said temporally-moving baseline value.

19. A sleep disorder breathing event counter as recited in claim 16, wherein said specified information is chosen from the group consisting of (i) the total number of counts accumulated in a specified time period, or (ii) the number of counts accumulated during each of a specified number of intervals comprising said time period.

* * * * *